US011120399B2

(12) United States Patent
Souffrou

(10) Patent No.: US 11,120,399 B2
(45) Date of Patent: Sep. 14, 2021

(54) SYSTEM AND METHOD FOR MANAGING MEDICAL DEVICE INVENTORY

(71) Applicant: Ashlea Souffrou, Grand Rapids, MI (US)

(72) Inventor: Ashlea Souffrou, Grand Rapids, MI (US)

(73) Assignee: SXANPRO, Grand Rapids, MI (US)

(*) Notice: Subject to any disclaimer, the term of this patent is extended or adjusted under 35 U.S.C. 154(b) by 215 days.

(21) Appl. No.: 16/275,071

(22) Filed: Feb. 13, 2019

(65) Prior Publication Data
US 2020/0258042 A1     Aug. 13, 2020

(51) Int. Cl.
*G06Q 10/08*     (2012.01)
*G16H 40/63*     (2018.01)
*G06F 16/22*     (2019.01)

(52) U.S. Cl.
CPC ......... *G06Q 10/0875* (2013.01); *G06F 16/22* (2019.01); *G16H 40/63* (2018.01)

(58) Field of Classification Search
CPC .. G06Q 10/087; G06Q 10/0875; G16H 40/63; G06F 16/22
USPC ...................................................... 705/28, 29
See application file for complete search history.

(56) References Cited

U.S. PATENT DOCUMENTS

| 8,645,156 B2 | 2/2014 | Ravazzolo |
| 9,250,712 B1 | 2/2016 | Todeschini |
| 9,990,603 B2 | 6/2018 | Kerrick |
| 10,013,669 B2 | 7/2018 | McCullough et al. |
| 10,152,688 B2 | 12/2018 | DeBusk et al. |
| 2003/0055753 A1* | 3/2003 | Dellar ............... G06Q 10/087 705/29 |
| 2008/0086387 A1* | 4/2008 | O'Rourke ........ G06Q 30/0601 705/26.1 |
| 2013/0087609 A1* | 4/2013 | Nichol ................ G06F 16/23 235/375 |
| 2014/0288952 A1 | 9/2014 | Smith et al. |

* cited by examiner

*Primary Examiner* — Allen C Chein
*Assistant Examiner* — Denisse Y Ortiz Roman
(74) *Attorney, Agent, or Firm* — Polsinelli PC

(57) ABSTRACT

A system for medical device inventory management is disclosed. The system is comprised of at least one scanner to scan medical device information associated with a medical device. The at least one scanner is in operable communication with at least one computing device configured to receive the medical device information from the scanner. A processor is in operable communication with the computing device and an interpreter adapted to transpose the medical device information to a graphical user interface. An inventory module is in operable communication with the processor to inventory the medical device information, including preparing a list of a plurality of medical devices. A document generator is in operable communication with the computing device to generate a document in a shareable format.

5 Claims, 6 Drawing Sheets

SYSTEM AND METHOD FOR MANAGING MEDICAL DEVICE INVENTORY

TECHNICAL FIELD

The embodiments generally relate to an inventory management and control system and, more specifically, to an inventory management and control system for the medical device industry.

BACKGROUND

Manufacturers, suppliers, and retailers alike each undergo the difficulty of managing inventory of their products. In the past, inventory was recorded manually leading to a significant loss of resources and a high propensity for errors. In recent years optical scanners have been used to identify product information and transmit the information to a readable medium.

While a variety of industries utilize various forms of electronic inventory management, the medical device industry has a low tolerance for errors throughout the inventory process due to the potential liability of harming a client due to inaccurate records.

Medical device inventory systems currently available are unable to scan and record the expiration date and lot number of a particular device in a standalone software package. This inability inconveniences various parties within the medical device industry including nurses, physicians, and medical device sales representatives and suppliers as users are required to utilize multiple software platforms to perform inventory tasks.

SUMMARY OF THE INVENTION

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

The embodiments described herein provide a system for medical device inventory management. The system is comprised of at least one scanner to scan medical device information associated with a medical device. The at least one scanner is in operable communication with at least one computing device configured to receive the medical device information from the scanner. A processor is in operable communication with the computing device, and an interpreter adapted to transpose the medical device information to a graphical user interface. An inventory module is in operable communication with the processor to inventory the medical device information including preparing a list of a plurality of medical devices. A document generator is in operable communication with the computing device to generate a document in a shareable format.

In one aspect, the medical device information is comprised of a unique device identifier, a lot number, an expiration date, a model number, and a manufacturer description.

In one aspect, the medical device information is comprised of a static part and a dynamic part. The static part is pulled from an external database. The external database may, in some aspects, be a Food and Drug Administration database.

In one aspect, the graphical user interface is comprised of a device details interface wherein medical device information is manually input.

Some embodiments provide for a method for facilitating the management of medical device inventory. The method comprises the steps of scanning, via a scanner in communication with a computing device, a plurality of medical device information associated with a medical device. The plurality of medical device information is comprised of a unique device identifier, a lot number, an expiration date, a model number, a catalog number, and a description. A processor may then interpret the medical device information and determine a static part and a dynamic part. The static part is pulled from an external database, and the dynamic part is interpreted by the interpreter. The medical device information is then logged into a database and displayed on the computing device.

BRIEF DESCRIPTION OF THE DRAWINGS

A complete understanding of the present embodiments and the advantages and features thereof will be more readily understood by reference to the following detailed description when considered in conjunction with the accompanying drawings wherein.

DETAILED DESCRIPTION

Figure 1:
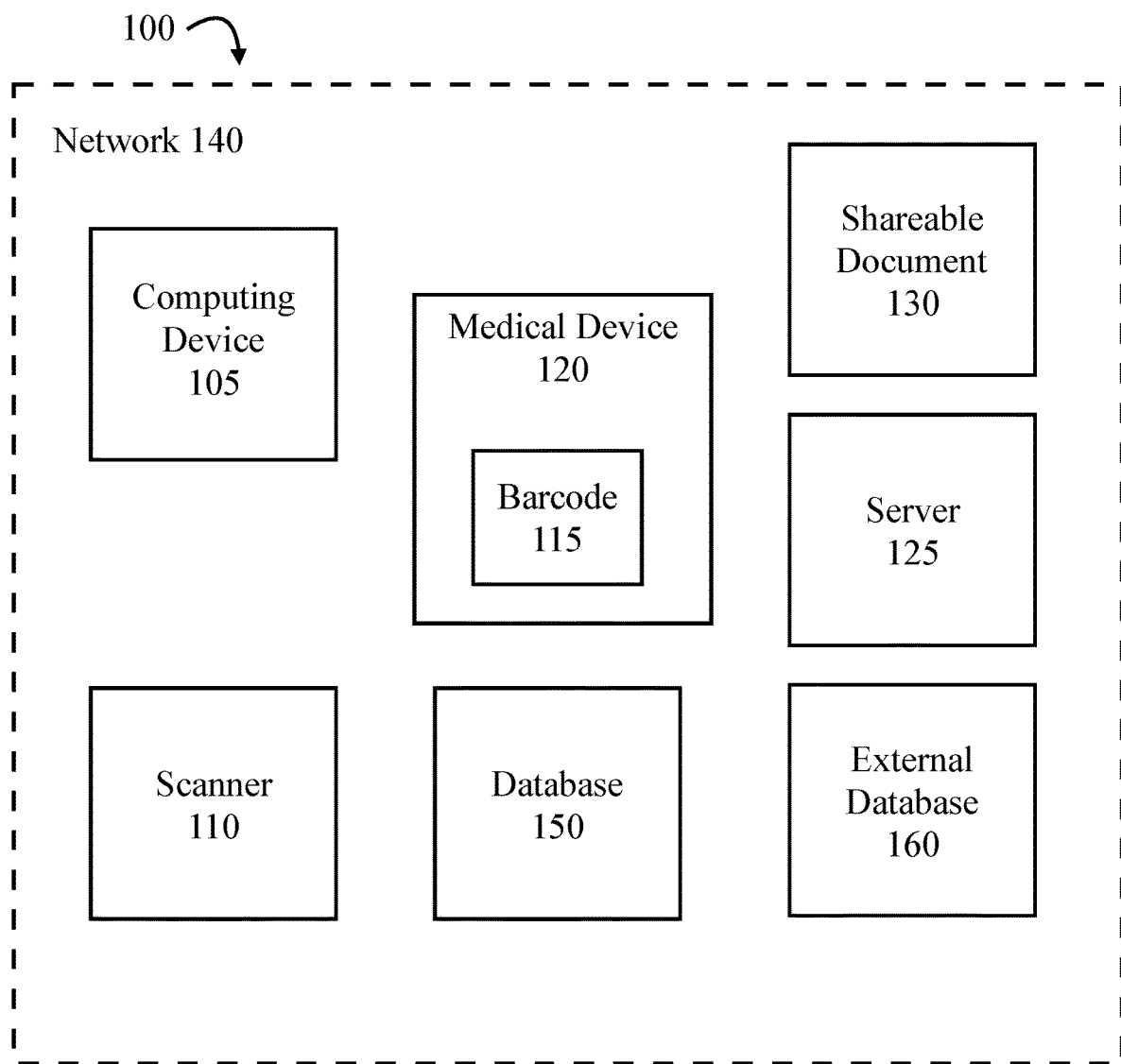
FIG. 1 illustrates a block diagram of the network infrastructure, according to some embodiments.

The specific details of the single embodiment or variety of embodiments described herein are to the described system and methods of use. Any specific details of the embodiments are used for demonstration purposes only, and no unnecessary limitations or inferences are to be understood therefrom.

Before describing in detail exemplary embodiments, it is noted that the embodiments reside primarily in combinations of components and procedures related to the system and method. Accordingly, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Some embodiments disclosed herein significantly improve the ability of medical device manufacturers, care providers, healthcare professionals, medical device suppliers, and medical device sales representatives to manage inventory. Aspects of the embodiments provide an improved service offering by providing functionalities either not present or in a more simplified form than is disclosed in the current arts of the medical device industry and similar product-based industries alike.

Some embodiments may provide an inventory management system configured to be applied to the medical device industry, a user interface for engaging with inventory data and data present in one or more external databases, such as the Food and Drug Administration (FDA) databases, and electronic data capture hardware and software systems.

As used herein, the term "medical device information" is used to describe any information provided on a medical device including, but not limited to, a unique device identifier (UDI), lot number, expiration date, model number, catalog number, a manufacturer name, and manufacturer description.

FIG. 1 illustrates an exemplary architecture of the inventory management system 100 implemented in the various embodiments disclosed herein. The system 100 is comprised of at least one computing device 105 in communication with a scanner 110. The scanner 110 may be integrated within the computing device 105 or provided as a separate hardware component as known in the arts. The scanner 110 reads a barcode 115 provided on the medical device 120 to determine the medical device information, such as a UDI, a lot number, an expiration date, a model number, a manufacturer, and a manufacturer description. A server 125 is operable to transmit, via network 140, the medical device information to the computing device 105, or to an external computing system to interpret the medical device information and transpose the medical device information into a shareable document 130 viewable on a printed medium, or on the graphical user interface of the computing device 105. Database 150 is configured to store medical device information and data associated with the system 100. In some embodiments, one or more external databases 160 may be utilized to aggregate and pull data. The external database 160 may be comprised of the Food and Drug Administration database, in addition to various additional external databases.

The computing device 105 may include conventional components such as one or more memory components and one or more processors. Examples of computing devices include such known mobile devices as smartphones, tablets, etc., but it should be understood that the computing device need not he a mobile device and the inventive concepts apply to other computing devices such as a desktop computer.

In some embodiments, the scanner 110 is any electronic data capture system with image scanning and/or barcode scanning capabilities as known in the arts. The scanner 110 may be specially adapted to scan and read barcodes provided on a medical device. In additional embodiments, the scanner 110 scans a barcode, QR code, and/or RFID tag to determine the information of the medical device. Once the medical device information has been determined, the system renders a visual of the medical device information on the graphical user interface (GUI) of the computing device 105.

The system 100 can include or be associated with a plurality of databases that include information for the system 100, inventory lists, and medical device information lists, generated by the system, which can be local, stored somewhere else and accessible using the network 140, generated as needed from various data sources, or some combination of these.

Figure 2:
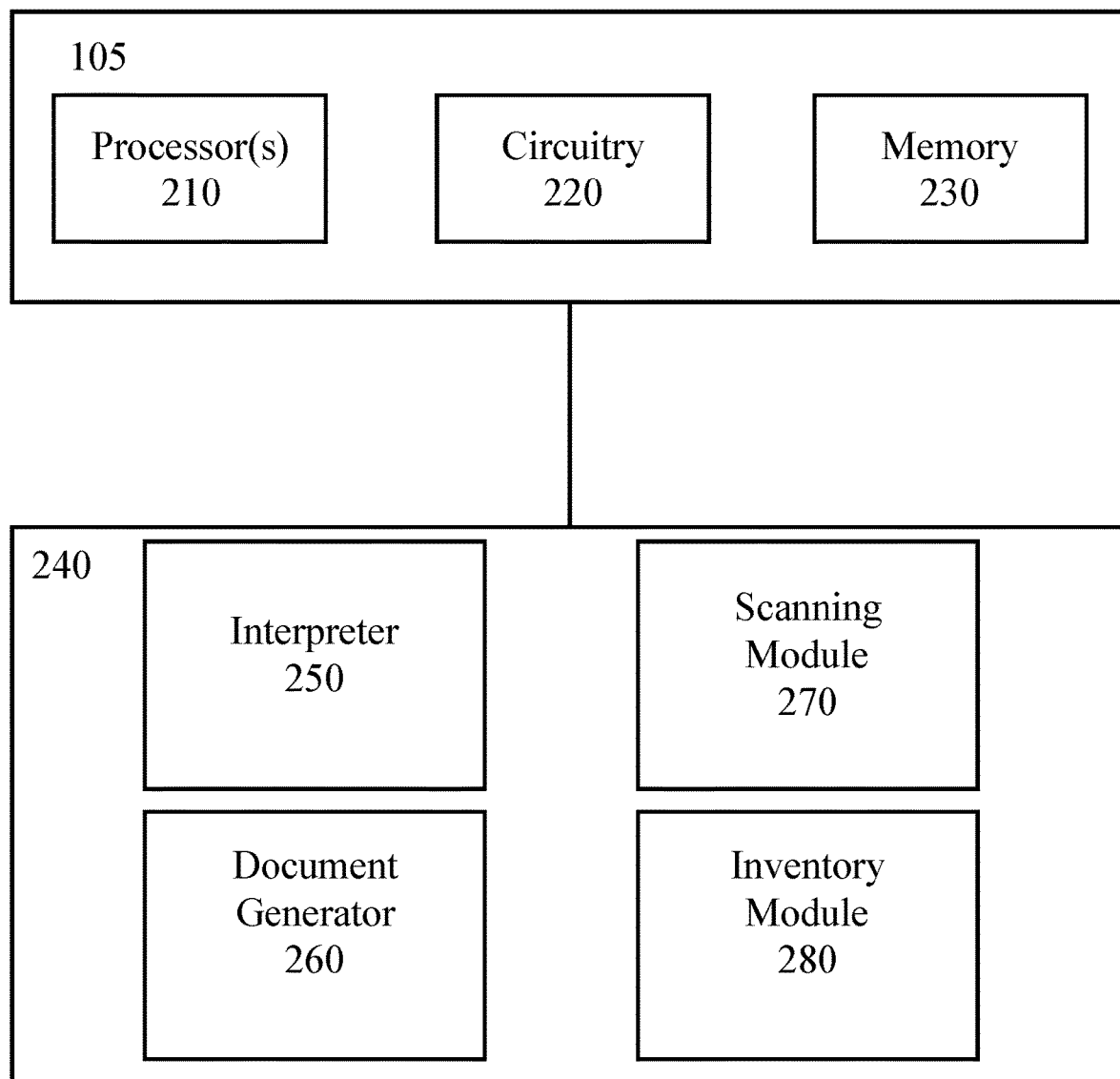
FIG. 2 illustrates a block diagram of the program logic and associated modules, according to some embodiments.

FIG. 2 illustrates a component level diagram of the computing device 105 utilized to perform the various embodiments disclosed herein. The computing device is comprised of at least one processor 210 connected via circuitry 220 to a memory 230 operable to perform program logic 240. The program logic 240 includes a plurality of code to perform various functions of the embodiments including an interpreter 250, a document generator 260, a scanning module 270, and an inventory module 280. In some aspects of the embodiments, the interpreter 250 receives medical device information from the scanning module 270 and interprets the information to create a list of medical devices using an inventory module 280. A document generator 260 operates to transpose the medical device information listed in the inventory module 280 to a shareable document format.

Figure 3:
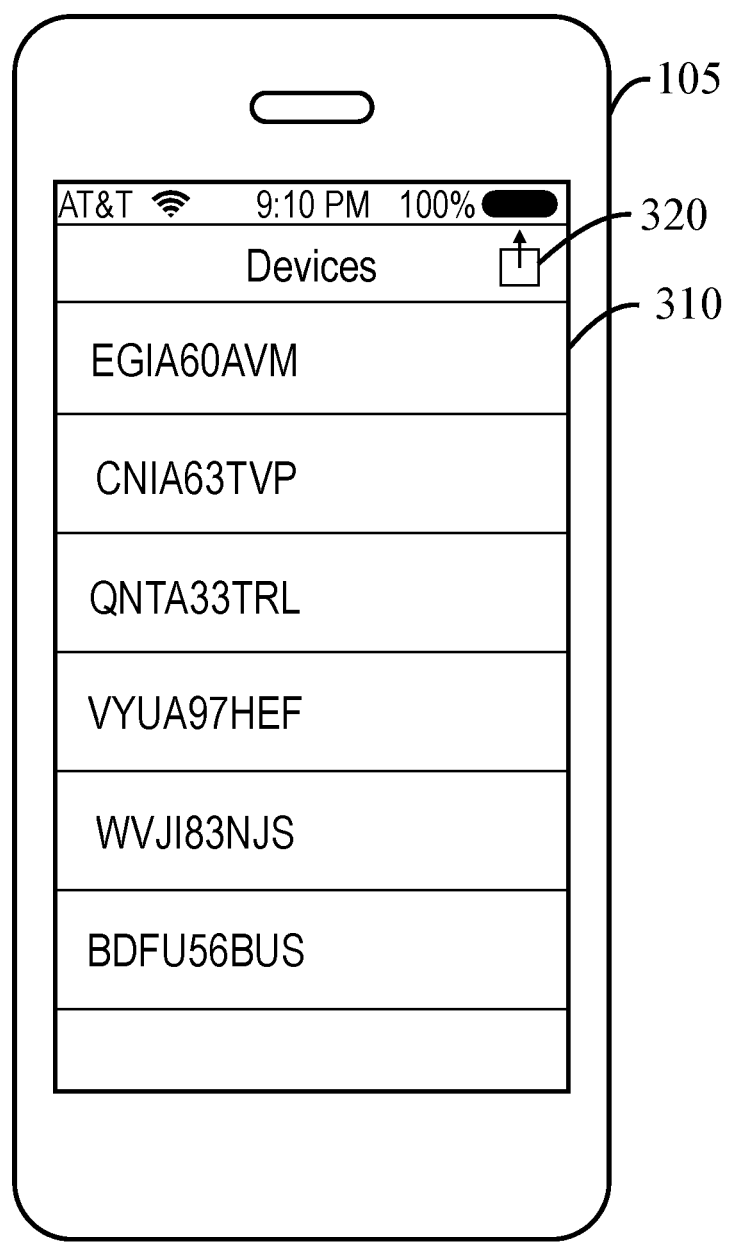
FIG. 3 illustrates a screenshot of the medical device inventory interface, according to some embodiments.

FIG. 3 illustrates a medical device inventory interface 310 displayed on the computing device 105. An export button 320 permits the medical device information displayed on the interface 310 to be transposed into a shareable document format, or exported to an external user via email or similar communications interface known in the arts.

Figure 4:
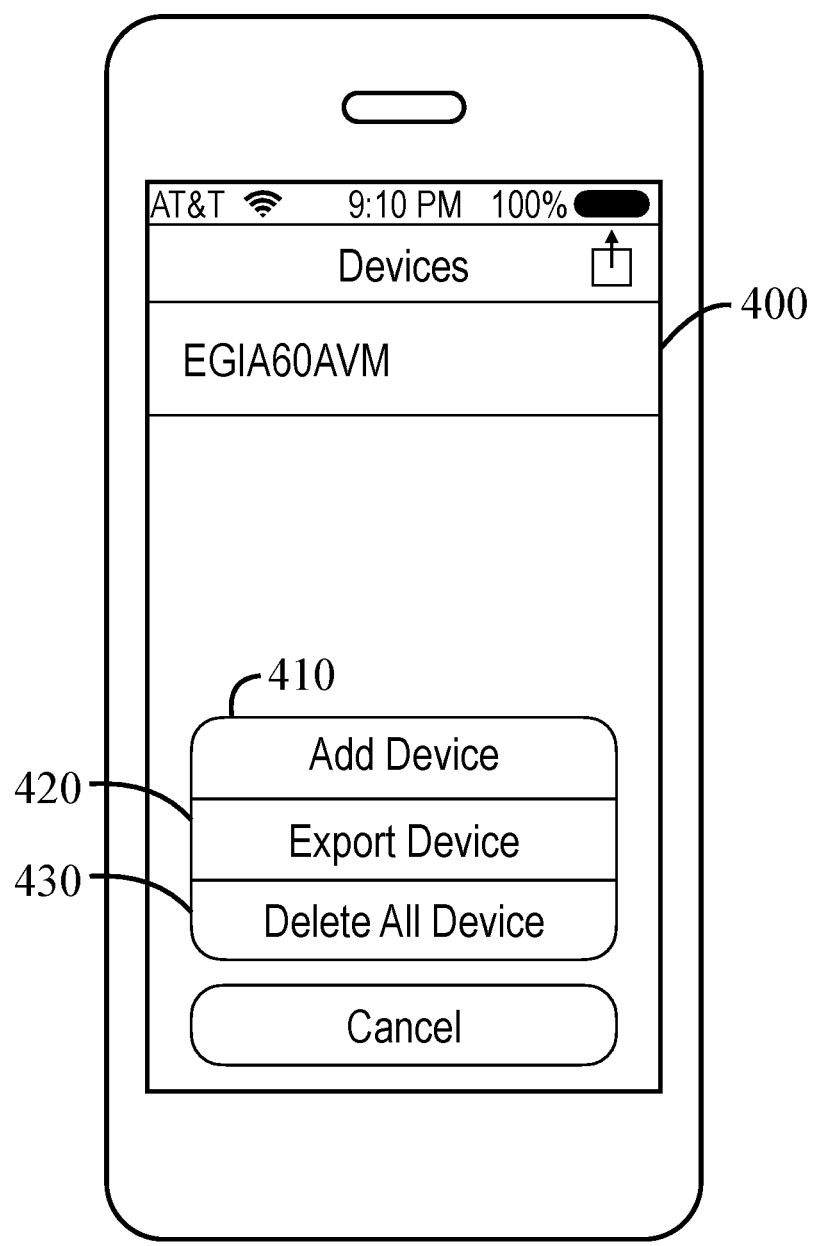
FIG. 4 illustrates a screenshot of the medical device input and export interface, according to some embodiments.
Figure 5:
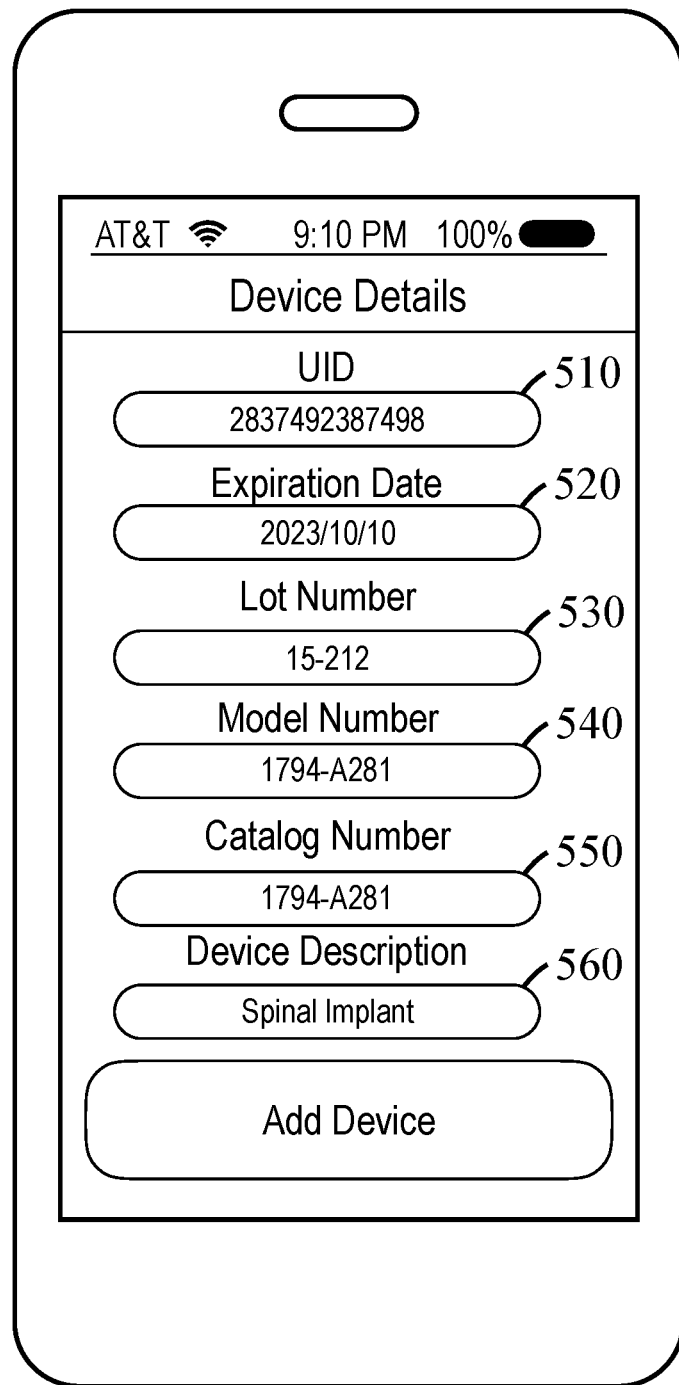
FIG. 5 illustrates a screenshot of the device details input interface, according to some embodiments.

FIG. 4 illustrates a medical device information export interface 400 which provides input buttons including an "Add Device" input 410, "Export Device" input 420, and a "Delete All Devices" input 430. Selecting the "Add Device" input 410 transmits the user to the device input interface illustrated in FIG. 5 wherein the user is provided with a plurality of input fields wherein the user inputs medical device information including a UID input 510, an expiration date input 520, a lot number input 530, a model number input 540, a catalog number input 550, and a device description input 560. Each input provided in FIG. 5 may be automatically entered using the scanner in communication with the interpreter as described hereinabove.

In some embodiments the medical device information export interface 400 may include input buttons such as, but not limited to, the manufacturer name, packaging type, quantity, price, and the ability for the input of a comment or other form of information or description of the medical device.

Figure 6:
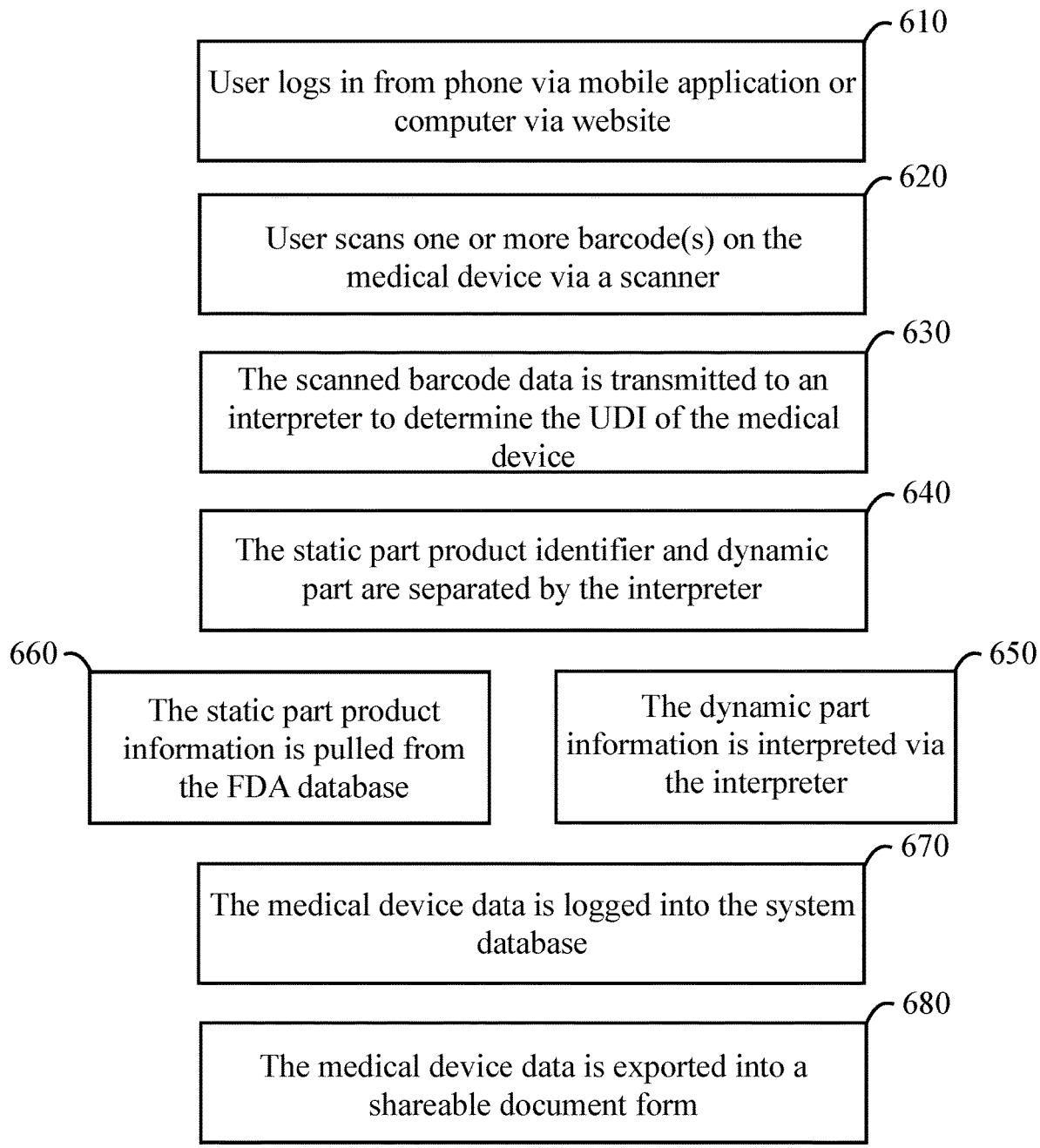
FIG. 6 illustrates a flowchart of a method of utilizing the medical device inventory management system, according to some embodiments.

FIG. 6 illustrates a flowchart of a method of using the system to manage medical device inventory. In step 610, the user accesses the system via the computing device and in step 620, scans the barcode on the medical device using the scanner. In step 630, the interpreter interprets the scanned barcode to identify the static part and the dynamic part of the barcode as shown in step 640. In step 650, the dynamic part is interpreted via the interpreter, and in step 660, the static part is pulled from an external database (such as the FDA database). In step 670, the medical device information is logged into the system database using the inventory module. Optionally, in step 680, the user may export the medical device information into a shareable document format.

The steps and/or actions of a system described in connection with the embodiments disclosed herein may be embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor such that the processor can read information from, and write information to, the storage medium. In the alternative, the storage medium may be integrated into the processor. Further, in some embodiments, the processor and the storage medium may reside in an Application Specific Integrated Circuit (ASIC). In the alternative, the processor and the storage medium may reside as discrete components in a computing device. Additionally, in some embodiments, the events and/or actions of a method or algorithm may reside as one or any combination or set of codes and/or instructions on a machine-readable medium and/or computer-readable medium, which may be incorporated into a computer program product.

Also, any connection may be associated with a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc," as used herein, include compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

Processors suitable for the execution of a computer program include both general and special purpose microprocessors and any one or more processors of any digital computing device. The processor will receive instructions and data from a read-only memory or a random-access memory or both. The essential elements of a computing device are a processor for performing actions in accordance with instructions and one or more memory devices for storing instructions and data. Generally, a computing device will also include, or be operatively coupled to receive data from or transfer data to, or both, one or more mass storage devices for storing data, e.g., magnetic, magneto-optical disks, or optical disks; however, a computing device need not have such devices. Moreover, a computing device can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive).

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that the present embodiment is not limited to what has been particularly shown and described hereinabove. A variety of modifications and variations are possible in light of the above teachings without departing from the following claims.

What is claimed is:

1. A computer-implemented system for medical device inventory management, the system comprising:
   at least one scanner configured to scan a barcode provided on a medical device for a first plurality of medical device information associated with the medical device, the at least one scanner integrated within a computing device configured to receive the first plurality of medical device information from the scanner, wherein the first plurality of medical device information comprises an expiration date, lot number, and a unique device identifier (UDI) for the medical device;
   a processor in operable communication with the computing device, the processor adapted to: interpret the first plurality of medical device information, via an interpreter; automatically pull from a local database a second plurality of medical device information associated with the medical device based on the interpreted first plurality of medical device information, wherein the second plurality of medical device information is stored on the local database comprising information from a Food and Drug Administration UDI database, the second plurality of medical device information comprising a model number and a manufacturer description; aggregate the first and second pluralities of medical device information, log the aggregated first and second pluralities of medical device information to a system database; and display a visual rendering of the aggregated first and second pluralities of medical device information that is viewable on a graphical user interface;
   an inventory module in operable communication with the processor, the inventory module operable to: prepare a list of a plurality of medical devices;
inventory the aggregated first and second pluralities of medical device information from the plurality of medical devices; and log the list of the plurality of medical devices and the inventory in the system database; and
   a document generator in operable communication with the computing device to transpose the inventoried aggregated first and second pluralities of medical device information from the system database to generate a document in a shareable format operable to be viewable on the graphical user interface and exported to an external user.

2. The system of claim 1, wherein the graphical user interface comprises a device details interface configured to receive manually inputted medical device information.

3. A method for facilitating the management of medical device inventory, the method comprising the steps of:
   scanning, via a scanner integrated within a computing device, a barcode provided on a medical device for a first plurality of medical device information associated with the medical device, the first plurality of medical device information comprising a unique device identifier (UDI), a lot number, and an expiration date;
   interpreting, via a processor in communication with an interpreter, the first plurality of medical device information;
   automatically pulling from a local database, via the processor, a second plurality of medical device information based on the interpreted first plurality of medical device information, the second plurality of medical device information comprising a model number and a manufacturer description, wherein the second plurality of medical device information is stored on the local database comprising information from a Food and Drug Administration UDI database;

aggregating the first and second pluralities of medical device information;

logging the aggregated first and second pluralities of medical device information into a system database;

preparing, via an inventory module in operable communication with the processor, a list of a plurality of medical devices;

taking inventory of the aggregated first and second pluralities of medical device information from the plurality of medical devices;

logging the list of the plurality of medical devices and the inventory in the system database;

displaying the aggregated first and second pluralities of medical device information via a graphical user interface on the computing device;

transposing, via a document generator, the aggregated first and second pluralities of medical device information from the system database into a document in a shareable format viewable on the graphical user interface; and exporting the document to an external user.

4. The method of claim 3, wherein the inventory module is operable to sort the aggregated medical device information and present the medical devices in an order.

5. The method of claim 3, further comprising the step of deleting all aggregated medical device information stored in the system database.

* * * * *